(12) United States Patent
Grabherr et al.

(10) Patent No.: US 8,367,041 B2
(45) Date of Patent: Feb. 5, 2013

(54) RADIOGRAPHIC CONTRAST AGENT FOR POSTMORTEM, EXPERIMENTAL AND DIAGNOSTIC ANGIOGRAPHY

(75) Inventors: Silke Grabherr, Murten (CH); Erich Gygax, Bern (CH)

(73) Assignee: Forim-X AG, Bern (CH)

( * ) Notice: Subject to any disclaimer, the term of this patent is extended or adjusted under 35 U.S.C. 154(b) by 628 days.

(21) Appl. No.: 12/441,822

(22) PCT Filed: Sep. 12, 2007

(86) PCT No.: PCT/CH2007/000446
§ 371 (c)(1),
(2), (4) Date: May 1, 2009

(87) PCT Pub. No.: WO2008/034270
PCT Pub. Date: Mar. 27, 2008

(65) Prior Publication Data
US 2010/0021389 A1   Jan. 28, 2010

(30) Foreign Application Priority Data

Sep. 18, 2006   (CH) .................................. 1485/06
Feb. 8, 2007   (CH) .................................. 0212/07

(51) Int. Cl.
*A61K 49/04*   (2006.01)
(52) U.S. Cl. ........................................ 424/9.4
(58) Field of Classification Search .................. None
See application file for complete search history.

(56) References Cited

U.S. PATENT DOCUMENTS

| 2,675,343 | A |   | 4/1954 | Clymer et al. |
| 6,498,273 | B2 | * | 12/2002 | Gabriel et al. ................ 564/153 |

FOREIGN PATENT DOCUMENTS

| DE | 26 02 907 B1 | 7/1977 |
| GB | 721264 A | 1/1955 |
| GB | 2 014 043 A | 8/1979 |
| WO | 92/18169 A1 | 10/1992 |
| WO | 97/24064 A1 | 7/1997 |

OTHER PUBLICATIONS

FLUX. Viscosity chart. Accessed online Jul. 13, 2011. http://pumplocker.com/images/lit/WEI1/FLUX-HIGH-VISCOSITY-B0000-VISC-CHART-1.PDF.*
Miller SW, Dinsmore RE, Wittenberg J, Maturi RA, Powell WJ Jr. Right and left ventricular volumes and wall measurements: determination by computed tomography in arrested canine hearts. 1997 AJR Am. J. Roentgenol. 129: 257-261.*
Kemp AR, Peters H. Viscosity of n-paraffin solutions. 1943 Ind. Eng. Chem. 35: 1108-1112.*
Jackowski C, Sonnenschein M, Thali MJ, Aghayev E, von Allmen G, Yen K, Dirnhofer R, Vock P. Virtopsy: postmortem minimally invasive angiography using cross section techniques—implementation and preliminary results. 2005 J. Forensic Sci. 50:1175-1186.*
Entry for magnesium stearate. Hawley's Condensed Chemical Dictionary. 2002 John Wiley and Sons, Inc. 14th edition.*
Savage Laboratories: "Ethiodiol (ethiodized oil) Injection", Daily Med-Internet Article, [Online] XP002431180, Retrieved from Internet: <URL:http://dailymed.nlm.nih.gov/dailymed/drugInfo.cfm?id=1812>, [Retrieved on Apr. 21, 2007] Beschreibung.
Silke Grabherr, et al., "Postmortem Angiography: Review of Former and Current Methods", Forensic Radiology Review, Mar. 2007, pp. 832-838, vol. 188, XP008078071.
Gates Corporation: "Viscosity Data", Internet Article, [Online] XP002431181, Retrieved from Internet: <URL://www.gates.com/brochure.cfm?brochure=2625&location_id=3046>, [retrieved on Apr. 21, 2007], Zelle 15 der Tabelle.
J. Barmeyer, "Post Mortem Coronary Angiography and Perfusion of Normal and Diseased Hearts, Perfusibility of Intercoronary Anastomoses", Beitr. Path. Anat., 1968, pp. 373-390, vol. 137, XP008078238.

* cited by examiner

Primary Examiner — Michael G Hartley
Assistant Examiner — Jennifer Lamberski
(74) Attorney, Agent, or Firm — Sughrue Mion, PLLC

(57) ABSTRACT

A contrast agent for angiography is disclosed, in particular, for examining animal or human bodies or components thereof such as members or organs thereof, comprising an essentially oil-based apolar contrast component for X-ray examinations, the contrast component having a contrast component viscosity in the range of 30-100 mPas. The contrast agent is characterised in that the contrast component is present in a mixture with at least one further apolar component, the viscosity of which is less than or at most equal to the contrast component viscosity. Methods for angiography examination are also disclosed, in which such a contrast agent or also a polar contrast agent are used at least periodically and applications of such contrast agents.

5 Claims, 14 Drawing Sheets a)

b)

c)

d)

a)

b)

c)

d)

c)

d)

Figure 1:

RADIOGRAPHIC CONTRAST AGENT FOR POSTMORTEM, EXPERIMENTAL AND DIAGNOSTIC ANGIOGRAPHY

CROSS REFERENCE TO RELATED APPLICATION

This application is a National Stage of International Application No. PCT/CH2007/000446 filed Sep. 12, 2007, claiming priority based on Switzerland Patent Application No. 2006-001485, filed Sep. 18, 2006 and 2007-000212, filed Feb. 8, 2007, the contents of all of which are incorporated herein by reference in their entirety.

TECHNICAL FIELD

The present invention relates to a contrast agent for postmortem angiography in particular for the examination of animal or human corpses or components thereof, e.g. of extremities or organs. The contrast agent therein contains an essentially oil-based, non-polar contrast component, as it is used for X-ray examinations, wherein the contrast component has a contrast component viscosity in the range of 30-100 mPas. The invention further relates to angiographic methods in which such a contrast agent is used at least during certain time intervals.

BACKGROUND ART

Angiography is the visualization of blood vessels by use of X-rays. For this purpose, a contrast agent, i.e. a substance, which is barely permeable for X-rays, is injected into the blood vessel. The radiographic image then shows the vessel's inner cavity filled with contrast agent. The resulting image is called angiogram. In medical language, the long word angiography is often shortened by the word angio. Computer tomography can also be used for angiography.

Computer tomography, of which the short form is CT, is the computer-assisted analysis of a number of radiographic images of an object, taken from different directions, in order to produce a three-dimensional image (voxel data). This is an imaging method.

The techniques currently used for image-producing vessel examination can be divided into three groups of methods: On the one hand casting techniques are available, on the other hand contrast agents exist, which are able to penetrate capillaries. A general overview of all techniques of postmortem angiography can be found in "Postmortem Angiography—A Review of Former and Current Methods" (S. Grabherr et al, AJR 2006 in press).

Casting Techniques:

For the casting techniques, for example methylmethacrylate (for example MERCOX® (methyl metharcrylate monomer solution (acrylic resin mixture)) or MICROFIL® (silicone rubber injection compounds), are used. These substances are injected, immediately after their mixing, after the vessels have been rinsed. After their hardening the tissue is macerated, which takes 2-4 weeks. What is then left over is the cast of the vessels, which can be analyzed by the naked eye, with the aid of a microscope or electron microscope, or also by radiographic techniques (see Djonov et al., Anal Embryo 2000; 202:347-357). Disadvantages of this method are the tedious manufacture of these preparations, the long time necessary for maceration and nonetheless the high risk of damaging the preparations by maceration and the subsequent handling, during which small parts of the preparation can easily break off.

Liquid Contrast Agents:

Most of the liquid contrast agents are not suitable for microangiographies. Water-based mixtures have the property to very quickly exit the vessel by penetrating the vessel's wall (so-called extravasation), which leads to diffuse contours of the represented vessels. Furthermore, their contrast is not high enough to clearly represent small vessels, such as capillaries.

Oily contrast agents have the property to remain intravasal without penetrating the vessel's wall (normally no extravasation). This leads to a clearly contoured image of the vessels. However, capillaries cannot be penetrated due to possible occlusions of the so-called capillaries [hair vessels].

Corpuscular contrast agents can be used for microangiography if small corpuscular particles are used. The most common corpuscular agent is MICROPAQUE® (barium sulfate-containing x-ray contrast agent). However, in its use in combination with micro-CT-devices, the problem of precipitation of the dissolved particles was described, which leads to artifacts (M. Marxen et al., Med Phys 2004, 31:305-313). Marxen clearly describes in his paper the necessity and the lack of a suitable contrast agent for microangiography using micro-CT.

SUMMARY OF THE INVENTION

An object of the invention thus is to provide an improved contrast agent for image-producing methods of the above mentioned type. It especially thus concerns the improvement of a contrast agent for angiography, for example for the examination of animal or human corpses or components thereof, e.g. of extremities (which may still be attached to the body), containing an essentially non-polar (in other words hardly or not miscible with water), that means usually oil-based contrast component for X-ray examinations. Therein, the contrast component in this type has a relatively high viscosity, typically in the range of 30-100 mPas.

The problem of such non-polar, oily contrast components is the fact, that they have a high viscosity. This high viscosity has the consequence that the contrast component cannot arbitrarily penetrate into capillaries and accordingly is also not able to completely represent the vascular system. In addition, it can lead to a real occlusion of capillaries and sections. The advantage of the essentially non-existent extravasation can thereby be reversed in numerous applications.

Surprisingly, it was determined, that such contrast components can be used very advantageously in a mixture. Therein, the mixture is characterized in that the contrast component is present in a mixture with at least one further non-polar component, of which the viscosity is lower or at the most equal to the viscosity of the contrast component. The admixing of this further non-polar component is used, on the one hand, in order to adjust the viscosity to the desired value, for example to the value of blood. On the other hand, it is used, in order to serve as a carrier for the contrast component, without changing the properties thereof concerning extravasation. This was especially unexpected with respect to the fact that the positive properties concerning extravasation can be maintained while nevertheless allowing the viscosity of the entire mixture to be adjusted to an optimal value, and that an excellent contrast is possible despite the dilution of the contrast component.

Preferably, the contrast agent is essentially free from water, meaning that it is not present as an emulsion. In other words, the mixture according to the invention preferably is a mixture, which only consists of non-polar components, wherein these components preferably can be essentially arbitrarily mixed among each other.

A first preferred embodiment is characterized in that the further non-polar component is an essentially saturated, branched, unbranched, or cyclic hydrocarbon, or a mixture of such hydrocarbons. Preferably, the further non-polar component is an alkane (preferably n-alkane, iso-alkane) or a mixture of alkanes, with a number of carbon atoms in the range of 5-45, especially preferably in the range of 12-30.

For example, it is possible to admix a non-polar component with a comparably low viscosity, such as for example an alkane with 12-18, preferably with 14-16 carbon atoms, or a mixture of such alkanes, wherein it preferably is an n-alkane or a mixture of such n-alkanes.

Therein, tetradecane or hexadecane are especially preferred, however, systems like cyclohexane or mixtures such as for example petroleum or even petroleum ether can also be used. Preferred systems have a melting point above 0° C. and/or a boiling point of at least 200° C.

Another preferred embodiment is characterized in that the further non-polar component is a component with a rather higher viscosity (but still at most equally high to that of the contrast component), such as for example an alkane, especially an n-alkane or also an iso-alkane, with 20-30 carbon atoms. Preferred is e.g. paraffine oil, especially paraffinum perliquidum. However, the non-polar component having a rather higher viscosity can also be a vegetable oil, such as for example a methylated rape oil or similar vegetable oils.

An additional preferred embodiment is characterized in that the contrast component has a viscosity in the range of 30-80 mPas. Thus, the contrast component for angiography preferably can be a iodine-based or sulphur-based radiographic contrast agent, especially preferably an iodized or brominated component or especially oil, for example a propyliodon, a fatty acid ethyl ester of iodized poppy-seed oil (e.g. LIPIODOL®), or iodipin, wherein it especially preferably is LIPIODOL® ultrafluid.

An especially preferred embodiment of the mixture is characterized in that the further non-polar component has a viscosity which is lower than the viscosity of the contrast component. The further non-polar component thus preferably has a viscosity in the range of 0.2-80 mPas, preferably in the range of 2-60 mPas.

As already mentioned, it is possible to admix a non-polar component with a comparatively low viscosity, thus preferably with a viscosity in the range of 1-10 mPas, preferably in the range of 2-4 mPas. Alternatively or especially preferably additionally (e.g. as a ternary or even multinary mixture), it is possible to admix a non-polar component with a rather higher viscosity (still lower than the viscosity of the contrast component), such as for example with a viscosity in the range of 25-80 mPas, wherein, as already mentioned, paraffinum perliquidum is especially preferred.

Therefore, for example a binary mixture of LIPIODOL® (ethyl esters of iodized fatty acids of poppy seed oil) ultrafluide, and tetradecane or hexadecane, or a binary mixture of LIPIODOL® ultrafluide and paraffinum perliquidum, or a ternary mixture of LIPIODOL® ultrafluide, tetradecane or hexadecane, and paraffinum perliquidum, is especially preferred.

Preferably, the contrast agent therein is characterized in that the volume ratio of contrast component to further non-polar component is in the range of 1:1 to 1:10, preferably in the range of 1:2-1:8, especially preferably in the range of 1:4-1:6.

For the angio-injection method and the angio-perfusion method, this is preferably the range for the volume ratio of a contrast component to a further non-polar component which has a rather higher viscosity (for example 25-80 mPas, see specifications above, corresponds e.g. to an alkane, especially an n-alkane or also an iso-alkane, with 20-30 carbon atoms, such as e.g. paraffine oil, especially preferably paraffinum perliquidum). The volume ratio of contrast component (or of contrast component already in a mixture with a further non-polar component of a rather high viscosity) to a further non-polar component with a comparatively low viscosity (for example in the range of 1-10 mPas, see specifications above, corresponds for example to an alkane with 12-18, preferably with 14-16 carbon atoms, or a mixture of such alkanes, especially preferably an n-alkane or a mixture of such n-alkanes, such as e.g. especially tetradecane or hexadecane) is best adjusted under consideration of the desired viscosity for the angio-injection method and the angio-perfusion method, resulting for example in ratios (contrast component: non-polar component with a comparably low viscosity) in the range of 20:1-100:1 or preferably 30:1-70:1.

For the so called angio-injection method preferably a ternary mixture is used, wherein the contrast component (e.g. LIPIODOL®) and a further non-polar component with a rather higher viscosity (e.g. paraffinum perliquidum, virtually as carrier) are used in a ratio in the range of 1:5, and subsequently the component with a comparatively low viscosity (e.g. hexadecane and/or tetradecane) e.g. in a ratio of 50:1 is used to adjust the viscosity of the entire mixture again depending on the radiographic contrast (radio-opacity) and the desired flow property.

Especially for microangio, mixtures of contrast component and non-polar component with a comparatively low viscosity (e.g. tetradecane or hexadecane) are used in a ratio of 1:4 or 1:6, wherein the quantity of the non-polar component is adjusted via the desired radio-opacity and the depth of penetration into small capillaries.

Furthermore, the present invention concerns a method for the dynamic angiographic examination of animal or human corpses or organs, or components, e.g. of extremities, thereof. The method is preferably characterized in that a contrast agent, e.g. as described above, is introduced into the vascular system and that subsequently or synchronously a radiograph is taken by the aid of x-rays, in particular a CT-image.

Furthermore, the present invention concerns a virtually dynamic method for the angiographic examination of animal or human corpses or organs, or components, e.g. of extremities thereof. This method is characterized in that first, a further non-polar component, as described above (or one or more polar components, such as e.g. water and/or polyethylene glycol) is essentially continuously introduced into the vascular system and circulated therein, and that during a time span of this non-polar component, a contrast component, as characterized above (or during the circulation of a polar component, one or more polar contrast components, such as e.g. on the basis of iopentole, methylglucamine ioxithalamate, iodixanole, iohexole, or similar), is added, wherein subsequently, synchronously or section-wise, radiographic images are taken by the aid of x-rays, especially a CT-image (so-called dynamic angiography, for example first arterial imaging, then parenchymal imaging, and then venous imaging, wherein paraffinum perliquidum, possibly in mixture with a decane (the term decane is to be subsequently understood as tetradecane and/or hexadecane) is used as a carrier, and a batch of contrast component is introduced). Generally, it is also possible, by the way, to colour the further component(s), such that e.g. a red colouring of the paraffinum perliquidum with sudan-red is possible.

The contrast agent for use in this method according to a first preferred embodiment thus can be a non-polar mixture, as described in detail above. However, it can also be an essentially polar mixture, which is preferably of an aqueous basis, and for which then a water-soluble contrast component or a contrast component which is emulsifiable in water is used. For the adjustment of the viscosity of such a mixture as a contrast agent, polar components having a high viscosity can be added. Such components can for example be polyols, such as e.g. long-chained sugars or long-chained glycols, such as e.g. polyethylene glycole (e.g. PEG 200 of Schärer und Schläpfer A G, Rothrist, C H). As a contrast component, e.g. Imagopaque 300 (iopentole, Amersham Health) then can be used. Here too, the desired viscosity of the contrast agent can then be adjusted by the additional polar component or its fraction in water, respectively. Typically, a viscosity of the contrast agent in the range of 0.5-60 mPas, especially preferably in the range of 0.1-50 mPas, especially preferably in the range of 20-45 or 30-40 mPas, is set for the applications according to the invention. In this case, the mixture thus preferably consists of an essentially polar contrast component (or a contrast component which is emulsifiable in water) and a further polar component, wherein this further polar component can either be present alone, if the desired viscosity can already be achieved thereby, or, however, as a mixture. If the further polar component is present as a mixture, preferably a system is used, in which a first further polar component with a low viscosity, preferably water, is used in combination with a second further polar component with a high viscosity, preferably a polyol. Thereby, the ratio between the first further polar component and the second further polar component can be used to adjust the viscosity of the contrast agent. This adjustment can preferably be carried out dynamically, which means that it is possible, just as for the application of the non-polar system described in detail above, to adjust the viscosity differently, by change of ratio of these two components, during the course of conducting the analysis, and thereby to visualize different areas of the vascular system during the course of the analysis.

Furthermore, the present invention concerns the use of a contrast agent, as described above, for the angiographic examination of animal- or human corpses or organs, or components, e.g. of extremities thereof.

According to another embodiment, a method is suggested, which is characterized in that a contrast agent, preferably in the form of a mixture, as the one described above, is introduced into the blood vessels in a non-pulsing manner. All measurements on the living body must be circulated in a pulsing manner, which is only not necessary on a corpse and opens essential additional analytical possibilities. Preferably, the contrast agent is introduced into the blood vessels under essentially constant pressure, or under a pressure varying temporally with a substantially lower or substantially higher rate than the naturally possible heart rate. Thus preferably, the circulation medium is not introduced in a volume-controlled, but in a pressure-controlled manner.

A further large analytical additional asset, which is not available from the natural analyses, is the possibility to circulate the contrast agent in the vascular system in the process at least section-wise against the natural flow direction of the blood. Possibly in combination with said pressure-control and the variation of further parameters which cannot be varied as much on the living body, incredible additional analytical possibilities are also established. Generally, additionally the difference of contrast agent introduced into the circulatory system and contrast agent exiting the circulatory system, concerning volume, pressure, temperature and/or component concentration, can be registered, and taken into account, preferably in a quantitative way, in the analysis. Thereby, for example the blood loss through an opening in the circulatory system can be quantitatively determined.

Generally, it is possible, in addition or alternatively, to vary the contrast agent during the introduction into the circulatory system in at least one of the following parameters, during and/or before the measurement, especially preferably depending on the image data obtained: temperature, mixing ratio, pressure. Prior to the introduction of contrast agent, the circulatory system can be rinsed, especially preferably by using a non-polar component or a (physiological) NaCl- or lactate-solution.

Furthermore, the present invention concerns a device for carrying out a method as described above. This device is preferably characterized in that means for pump-driven introduction of contrast agent into the circulatory system are provided, as well as means for the recording and quantitative registration of contrast agent exiting the circulatory system after circulation.

Alternatively or in addition, the device can be characterized in that a unit is provided, with which, prior to the introduction of the contrast agent into the circulatory system, the contrast agent is either admixed in an automated way in a desired ratio of contrast agent and one or more further non-polar (or polar) component(s), possibly in a temporally dependent fashion, and prepared for the introduction, and/or the contrast agent is adjusted in its temperature.

Further preferred embodiments of the present invention are described in the dependent claims.

SHORT DESCRIPTION OF THE FIGURES

Figure 2:
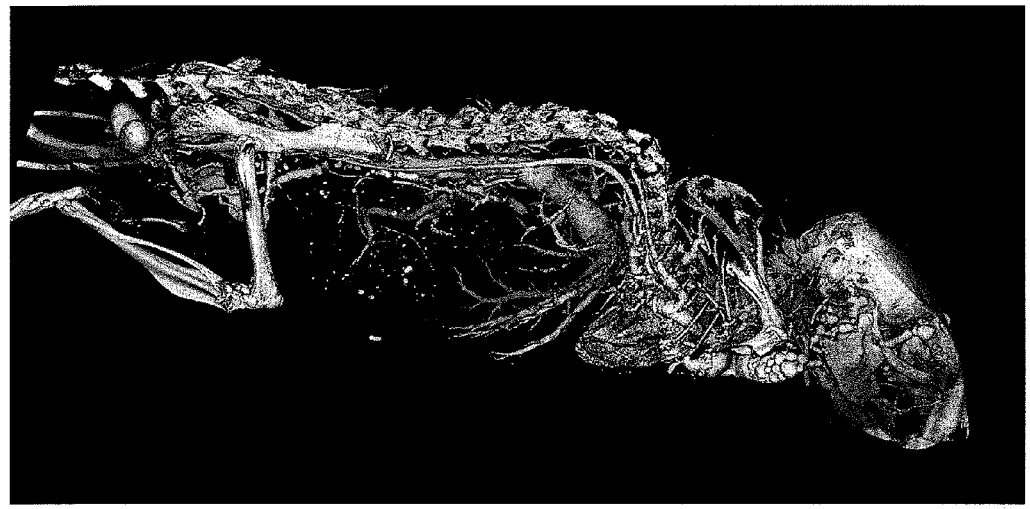
Figure 3:
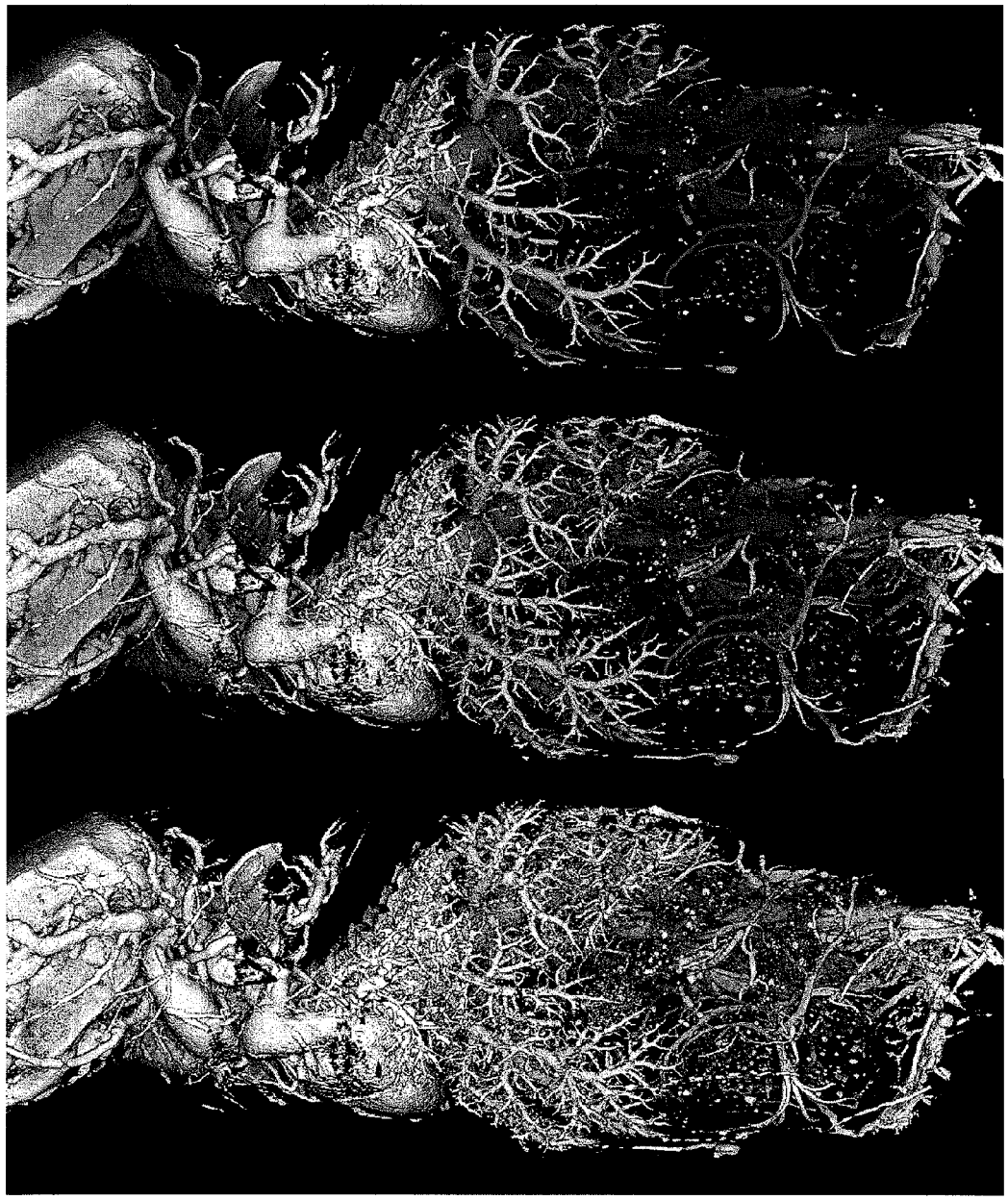
Figure 4:
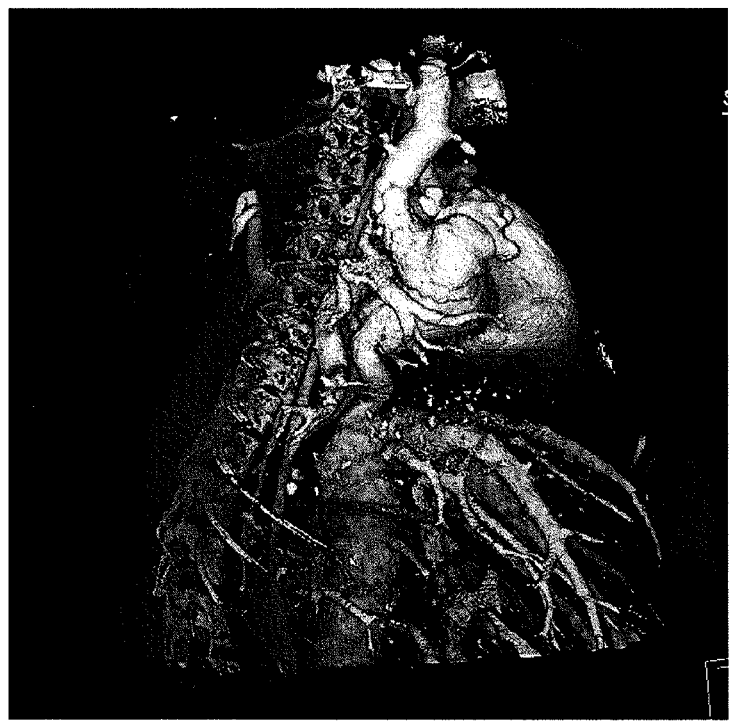
Figure 5:
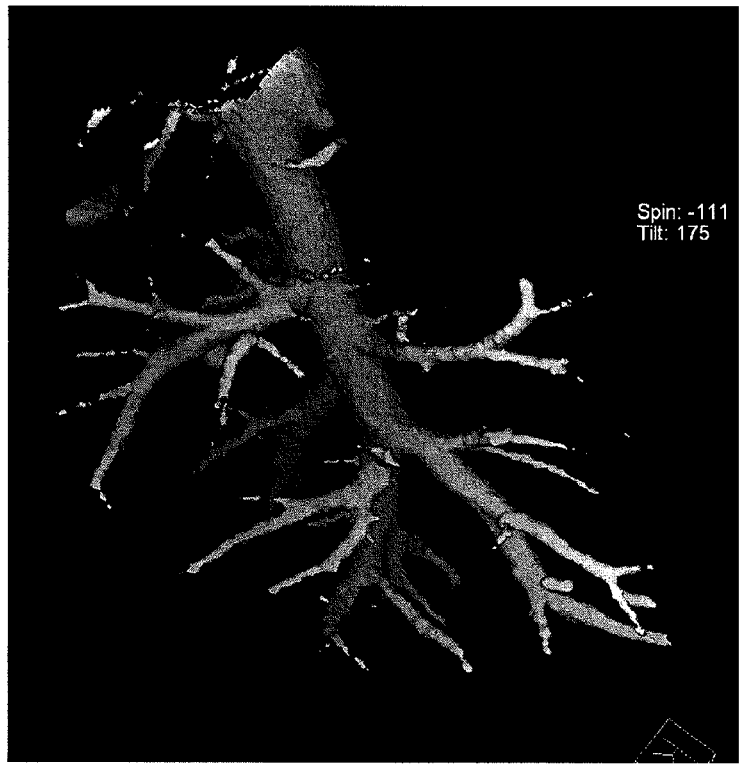
Figure 6:
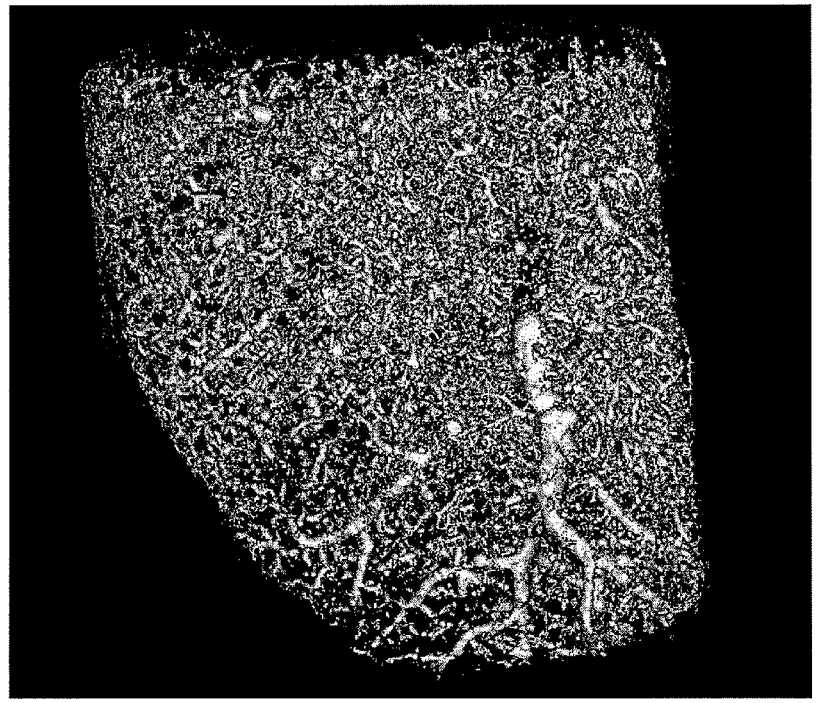
Figure 7:
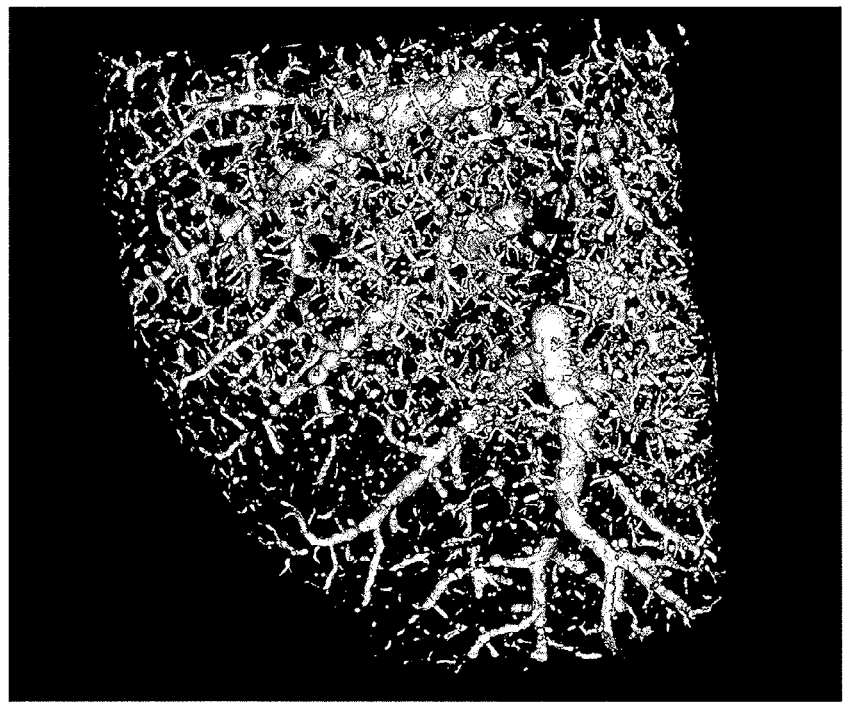
Figure 8:
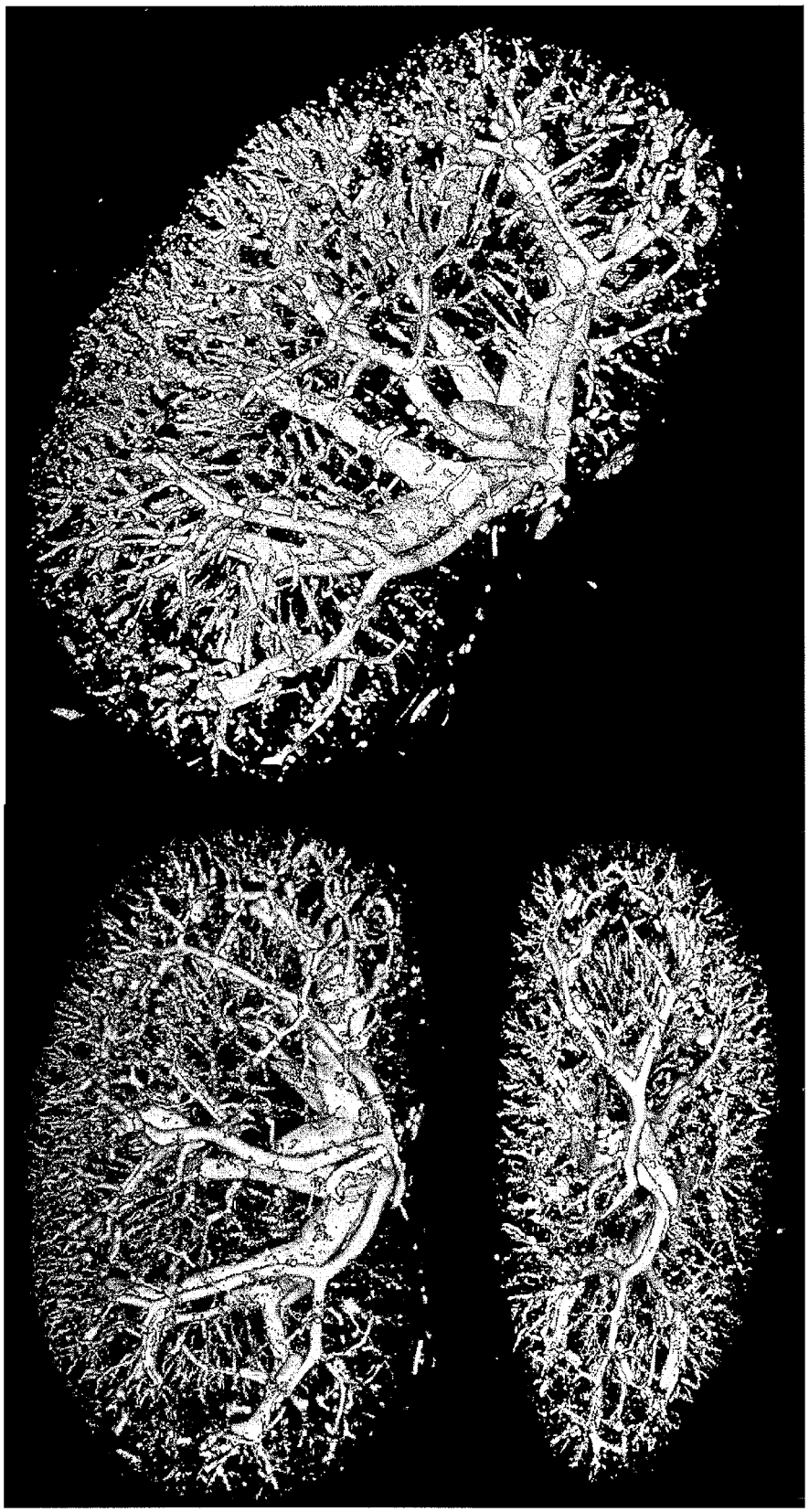
Figure 9:
Figure 9:
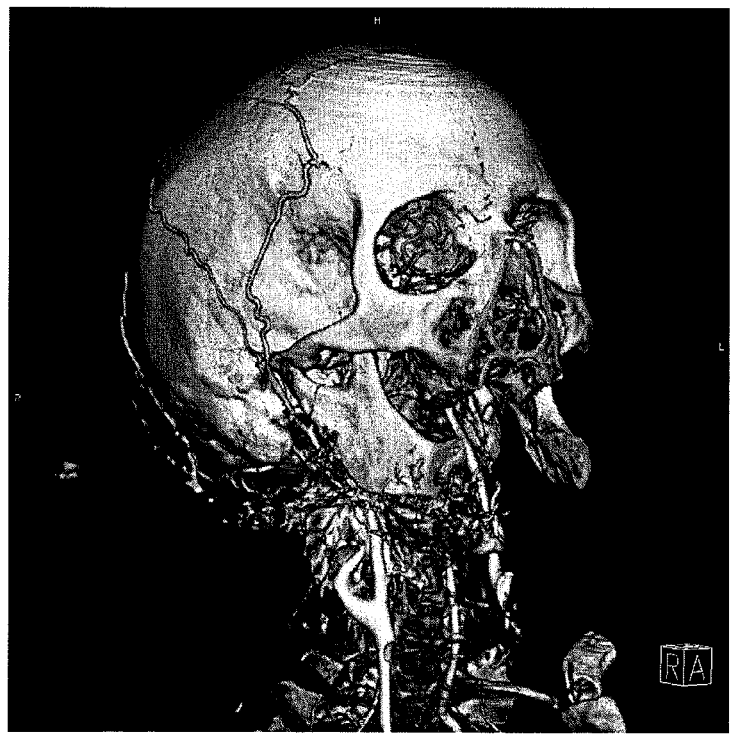
Figure 9:
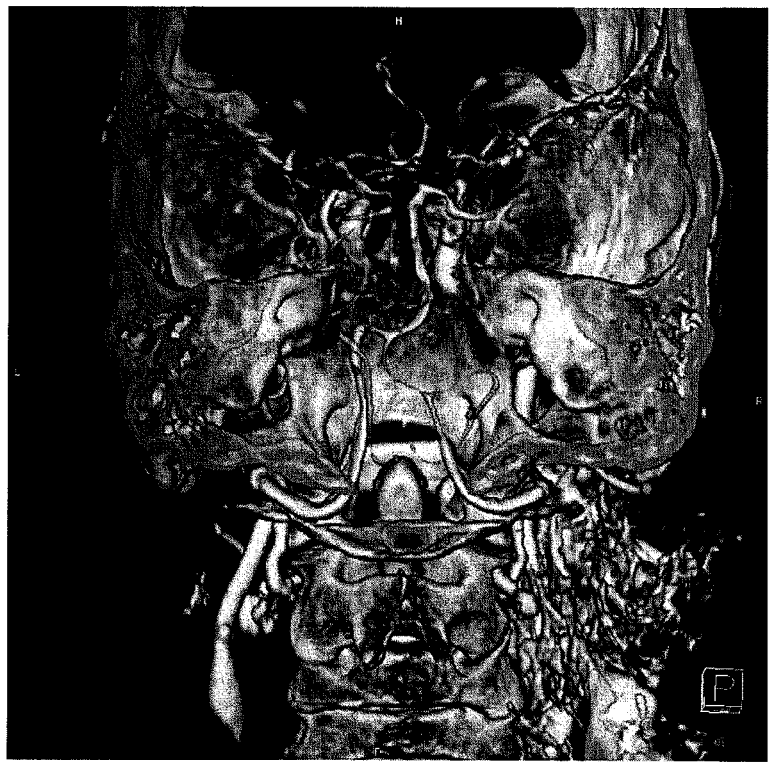
Figure 9:
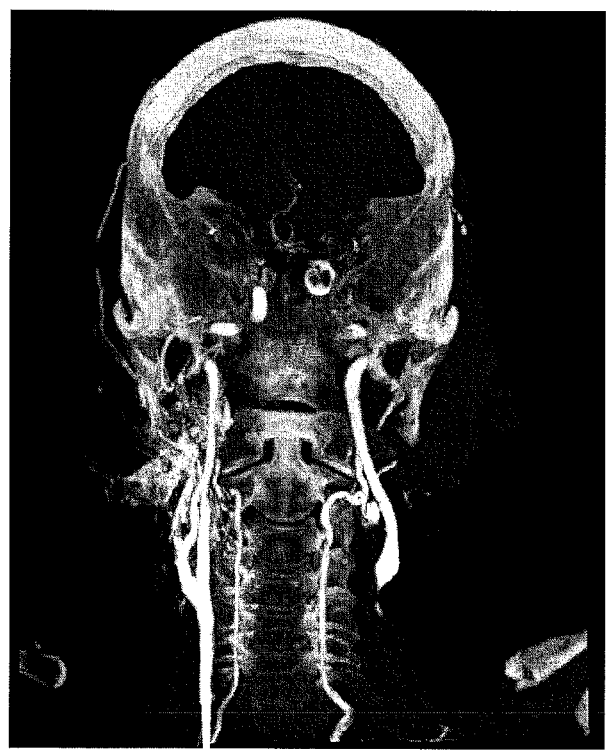
Figure 10:
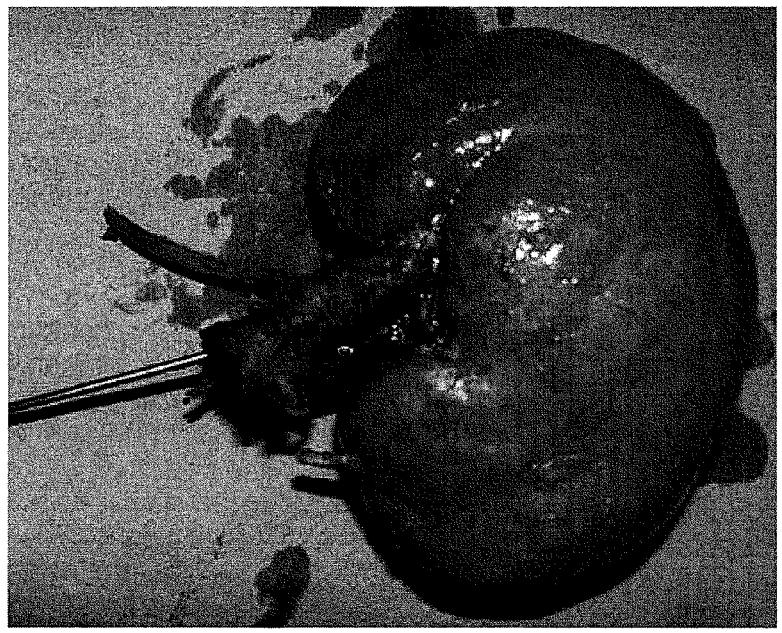
Figure 10:
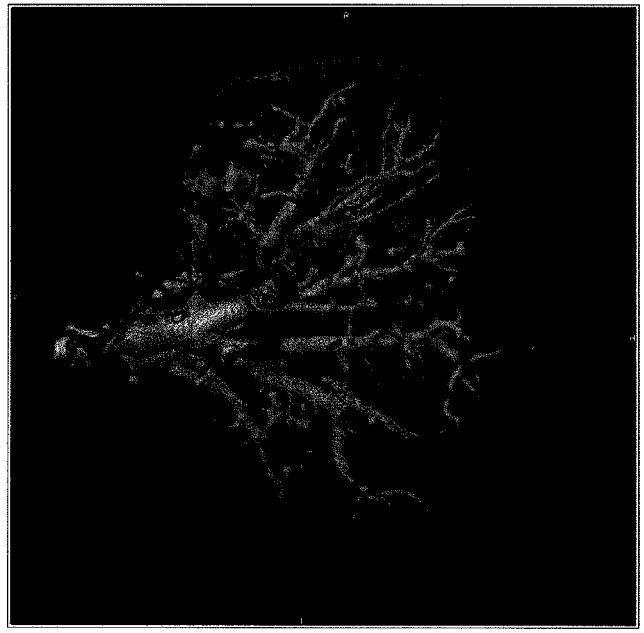
Figure 10:
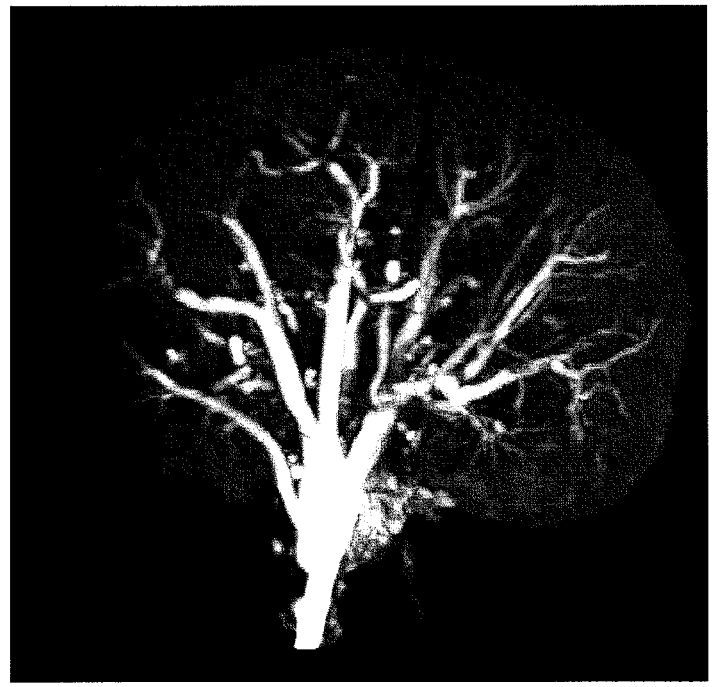
Figure 10:
Figure 11:
Figure 12:
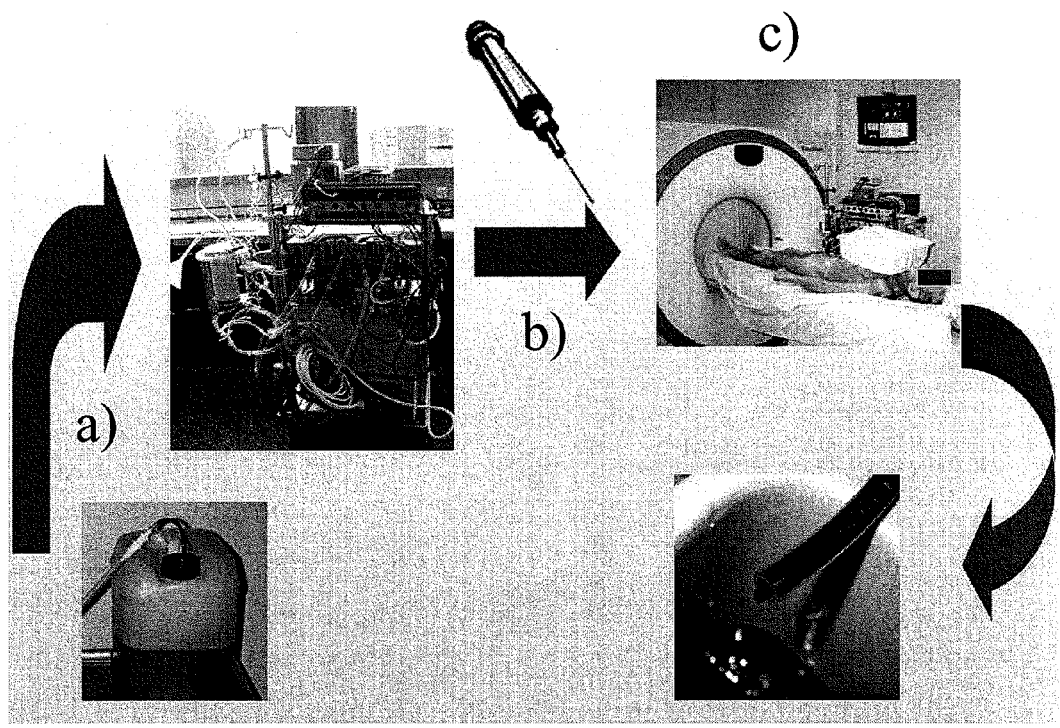

The invention shall subsequently be further explained using some examples in connection with the drawings, wherein are shown:

FIG. 1: a post-mortem micro-CT-scan of a mouse, with a representation of the large vessels;

FIG. 2: a better overview of the large vessels of the entire body after removal of the ribs and front legs at the work station (virtual scalpel);

FIG. 3: a visualization of the smaller vessel-branches by changing the windowing at the work station;

FIG. 4: a representation of the heart and the liver vessels after virtual editing of the data of a partial body scan of a mouse;

FIG. 5: a representation of the main branches of the kidney vessels after virtually cutting the organ out of a partial body scan;

FIG. 6: a high-resolution scan of a lung assay of a mouse with 3D-representation of smallest vessels;

FIG. 7: a better view of the main branches of the lung vessels of an image according to FIG. 6 with the same data set by changing the windowing;

FIG. 8: different representation possibilities of a kidney from the data set of a high-resolution single organ scan;

FIG. 9: shows the angio-injection method on a human corpse, wherein in a) the access of the contrast agent via re A. carotis communis is shown, and b)-d) show different views of the CT-images on the head of the examination object;

FIG. 10: shows the angio-injection method on the single organ (human kidney), wherein in a) the access of the contrast agent via A. renalis is shown, and b)-d) show different views of the CT-images of the scan of the kidney;

FIG. 11: shows the angio-injection method on the lower extremity of a human corpse, wherein the access is opened via A. femoralis superficialis, and different representations of the leg are shown;

FIG. 12: shows a schematic representation of the angio-perfusion method; and

Figure 13:
Figure 13:
Figure 13:
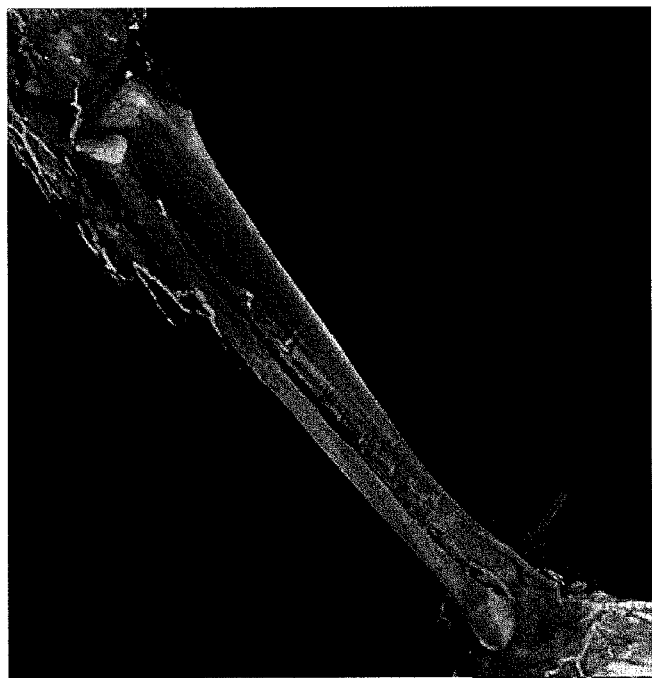
Figure 13:
Figure 13:
Figure 13:

FIG. 13: shows CT-images of a corpse, which suffered from PAOD (Peripheral Arterial Occlusive Disease), wherein in a) and b) the generally very poor perfusion in the area of the lower leg can be recognized, in c) the lower area of the lower leg with PAOD, and in d)-f) the corresponding specific localization of an occlusion.

DETAILED DESCRIPTION OF THE PREFERRED EMBODIMENTS

The suggested contrast agent can be used, for example, for microscopical vessel research (so-called microangio), but also for the angio-injection method or for the angio-perfusion method.

The preferred mixtures for these three methods are as follows:
Microangio: LIPIODOL®+decane (hexadecane or tetradecane), for example at a ratio of 1:4;
Angio-injection method: LIPIODOL®+paraffinum perliquidum+possibly decane, for example at a ratio of 1:5 and decane until the desired viscosity is reached;
Angio-perfusion method: Perfusion with paraffinum perliquidum, possibly supplemented by decane according to the desired viscosity, bolus injection of LIPIODOL® into the existing and continuing circulation.

After we have successfully used oily perfusates and contrast agents on animal cadavers and human corpses within the scope of the development of a minimally invasive, postmortem angiography, an unexpectedly advantageous new mixture for the use of a postmortem angiography using micro-CT was developed on this basis. In contrast to our previously used oily liquid, this new mixture does not lead to micro-embodies of the capillary system (S. Grabherr at al, A.IR 2006 in press) but to the penetration and thereby to the representation of this area of the vascular system.

Components:
1. LIPIODOL® ultrafluide. (Guerbert, France) [0056]
2. Tetradecane (Tetradecane olefine free, Fluka, Switzerland) or hexadecane (Hexadecane, Fluka, Switzerland)

The composition of these components can be varied. The oily contrast agent Lipiodol Ultrafluide® provides for a high contrast (about 2000 HU), while the decane serves as a diluent which allows the penetration of capillaries. The more decane is used, the lower the viscosity becomes, and the smaller the vessels which can be visualized.

As mixtures already successfully used, a ratio of LIPIODOL®:decane of 1:4 and 1:6 are advisable.

Advantages of the new contrast agent (essentially for all the three methods mentioned above):

Practical ways of handling: one of the probably most essential advantages of this contrast agent mixture is the easy handling. A simple injection into the vascular area to be visualized is enough.

Durability of the assays: Because the oily contrast agent remains intravasal, the assays can be stored for several days after injection and only then examined.

Transportability of the assays: The long durability of the assays allows the transport between laboratories (e.g. injection in Berne, examination and analysis in the USA).

Repeated examination possibilities: Multiple scans and analyses of an assay are possible, which is essential in the case of ambiguous findings.

3D-reconstruction with "zoom-in" and virtual assay editing: With the help of the examination with micro-CT, besides the two-dimensional reconstruction, also a three-dimensional reconstruction of the data is possible. By zoom-in and virtual cutting of the assays, arbitrary areas can be enlarged, cut out and represented, without destroying the assays.

Quantification: Special software already existing e.g. for the measurement of bone density for micro-CT-applications, can very easily be adapted for the quantification of the high-contrast vessels.

Selective, caliber-dependent representability: Depending on the mixing ratio, different vessel sections can be represented according to their caliber. It is thus possible to selectively visualize only large supply vessels or also capillaries.

Possibility of dynamic angiography: In case of a corresponding injection technique, a precise determination of the arterial, venous and capillary phase is made possible, in analogy to clinical angiography.

Possibility of repeated injection: When carrying out a dynamic angiography, a rinsing-out of the contrast agent from the vascular system is possible due to a lack of loss of contrast agent to the surrounding tissue, which enables a repeated injection without a falsification of the results by remainders of the previous injection. This is important, if ambiguous findings appear in a phase of dynamic angiography.

Possibility for further examinations: The examined organs can be embedded and additionally be examined morphologically (paraffin embedding and examination by electron microscopical section examination). This is important if the 3 D-structure correlates with the tissue morphology and shall be compared.

EXPERIMENTAL PART

Microangiography (Microangio)

For this method, a mixture of LIPIODOL® and decane was injected as contrast agent (KM) into the vascular system of a dead mouse, followed by the performance of a micro-CT with a device of the type "Siemens Micro-CT-Scanner".

Preliminary Test to Evaluate the KM in the "Live Scanner":
Scan KM (LIPIODOL®: decane=1:4) in 0.8 mm Venflon (butterfly needle/permanent venous catheter [Verweilkanule]): KM is clearly visible.

Mouse 1:
KM (LIPIODOL®: decane=1:4) from below into the V. cava inf.; scan of the anterior/upper part of the body only.

Mouse 2:
KM (LIPIODOL®: decane=1:6) from below into the V. cava inf.; no scan of the complete mouse; organ removal for isolated organ scans:
heart
liver
kidney
head Mouse 3:
KM (LIPIODOL®: decane=1:6) from below into the V. cava inf.; injection KM (LIPIODOL® decane=1:6) into right V. saphena; 3 scans for whole body representation.

Mouse 4:
Injection KM (LIPIODOL®: decane=1:6) into left ventricle; scan of anterior part of body only.

Mouse 5:
Injection KM (LIPIODOL®: decane=1:6) aorta (small amount) and V. cava inf.; 2 scans (head and thorax).

Mouse 6:
Injection KM (LIPIODOL®: decane=1:6) from below into the V. cava inf.; 2 scans (head and thorax).

Mouse 7:
Injection KM (LIPIODOL®: decane=1:5) into V. porta;

Organ removal for single scans:
 liver lobes (upper, incl. gall bladder)
 heart
 right and left kidney.

Different reconstructions from the data set of the micro-CT scans mentioned above are shown in FIG. 1-8. From the figures, is can be seen that the contrast agent on the one hand allows a high resolution, and on the other hand an excellent penetration, even into smallest vascular systems.

Angio-Injection Method:

Herein, a manual injection of iodine-containing contrast agent LIPIODOL® was carried out in assays of corpses fixated by formalin for 2 years, whose vessels were occluded with fixated blood.

Preparation with a dilution series of KM, wherein LIPIODOL®: paraffin oil (each time as paraffinum perliquidum) 1:1, 1:5, 1:10, and 1:20 were examined. The following angiographies were performed with 1:5, because this showed the best compromise of viscosity, contrast effect and vessel penetration for the aspired visualization.

Mixing of the contrast agent: LIPIODOL®: paraffin oil=1:5. Per 500 ml of this mixture, additionally about 10 ml of decane. After injection of the contrast agent mixture, multi slice-CT with data reconstruction as MIP and VRT.

FIGS. 9-11 show the thus obtained images from the angio-injecting method on the one hand, of the head area (FIG. 9), of a kidney (FIG. 10) and of a leg (FIG. 11), wherein it can be recognized how the used contrast agent allows an excellent contrast and despite the previously stored blood clots, an excellent penetration into the blood vessels, without any substantial extravasation being recognizable.

3. Angio-Perfusion Method:

Angio-experiment on the human corpse, body: anatomy-corpse after Till-fixation, injuries already present (state after operation on left knee and an open tibia fracture on the right)
 Method (see schematic representation in FIG. 12):
 Cannulation in the right groin (A. femoralis, V. femoralis).
 Perfusion with the aid of a heart-lung machine (perfusate: paraffin oil+decane at a ratio of about 500 ml : 10 ml). Perfusion speed 5-10 ml per kg bodyweight / min. See a) in FIG. 12.
 Addition of the contrast agent Lipiodol® (40 ml) into the perfusate (injection into the tube that leads to the artery, within a time span of a few seconds (bolus injection). See b) in FIG. 12.
 CT-scans. See c) in FIG. 12.
 Result: Successful perfusion (filling of the varices on the legs, filling of the A. Carotis); contrast in the CT.

The results of the perfusion can be recognized in FIGS. 13 *a-f*. The examined corpse suffered from PAOD (Peripherial Arterial Occlusive Disease) prior to death, while FIGS. 13*a*) and b) show the generally very poor perfusion in the region of the lower leg, FIG. 13*c*) shows the lower area of the lower leg with PAOD, and the Figures d)-f) show the according specific localization of an occlusion.

Contrast agent can either be injected as a bolus or added in higher quantity, wherein for dynamic angiography, a bolus should be introduced within a time-span as short as possible. Longer tubes of the heart-lung-machine are advantageous for a whole body scan, in order to compensate for the movement of the CT-table (typ. about 3 m).

Summary:

The new contrast agent allows a reliable, fast and repeated examination and representation of 2D and 3D vessel architecture of laboratory animals (e.g. microangiography with micro-CT), as well as postmortem on the human and animal corpse (angio-injection method). Furthermore, it allows dynamic imaging and quantification of the "blood loss" by the use of the angio-perfusion method. Practical handling, quantification possibilities, and exact representation of different vascular parts will establish this method as a standard examination in the evaluation of genetically manipulated laboratory animals, pharmacological and toxicological studies and of genetically engineered products. This new visualization and quantification method shall replace the old, reliable, however very time-consuming and highly specific techniques and pave the way for a comprehensive, simple, practical and uncomplicated application.

Below, the machine concept of the post-mortem angiography shall be described with the aid of a modified heart-lung-machine. The machine concept is based on two angiography methods, which can optionally be carried out in a stationary (in a forensic department) or mobile manner. The design of the heart-lung-machine is concipated this way, such that stationary as well as mobile postmortem angiographies can be carried out. As a basic device of such a heart-lung-machine, for example the device distributed by Maquet, or Jostra, respectively, can be used. With the name Jostra HL 20 MECC CONSOLE.

Components of the machine concept: the machine concept of the modified heart-lung-machine contains six basic components (machine scaffold, power supply, drive unit, control unit, computer unit as well as expendable material), which will each be described below.

Machine scaffold: The machine scaffold consists of two base plates (lower, upper), four steel tubes, as well as two rear transverse bracings for stabilization purposes. On the lower steel base plate, a drive rack is integrated. The drive rack with four wheels can be arrested and is rotatable around the longitudinal axis.

Power supply: Principally, the modified heart-lung machine is supplied with power via an external source. Usually, the machine is supplied with 220V or 110V. The power converter contains batteries, which ensure a line current-independent operation of 120 minutes (maximal capacity).

Drive unit: the drive unit consists of a double-V-belt-driven roller pump or peristaltic pump. The roller pump is connected with the power converter via a plug connection. For the mobile model, said additional battery unit is provided. This way, only the pump alone can be operated, which allows an additional field of application (Single Shot Angiography) without a computer unit, and also a static angiography-process. For the dynamic angiography, the roller pump is connected with the control- and computer unit. This connection allows a form of angiography, which can be carried out in a pressure- as well as in a volume-controlled manner (see below). Furthermore, it is possible, to provide means (e.g. flow-through heater etc.), by which the circulation medium is heated or cooled prior to and/or after the circulation. The roller pump provides the possibility of occlusive adjustment, in order to ensure a pressure-controlled postmortem perfusion.

Furthermore, optionally, a unit can be provided, which automatically mixes the contrast agent introduced into the corpse from starting materials, as described above (contrast component, further apolar component(s), etc.) in a controlled manner. This mixing can of course also be carried out in a time-dependent and process-dependent fashion, in order to allow a real dynamic process management concerning the contrast agent composition. The control of this mixing unit can be carried out by the control unit discussed below.

Control unit/user module: In order to answer the defined questions (quantity, occlusion, etc.), the pump contains at least four possible settings (³⁄₁₆-, ¼-, ⅜- and ½-inch), via which by the aid of the determinants, number of revolutions, and tube diameter, the searched-for volumina can be calculated and graphically represented (whole body perfusions or selective organ perfusions). The integrated pressure control additionally allows directed conclusions about occlusion rates of defined vessel parts. Furthermore, the roller pump can also be operated in the so-called lt. or ml/min mode, which additionally allows defined conclusions about volume losses.

Control unit: The control unit consists of a screen-like user module, as well as electric modules, which are fastened to the upper base plate. The user module of the control unit serves for the power line- and battery control and the activation of the pressure- and volume modes.

The electric modules are connected with the computer unit. The electric modules contain a pressure registration and a volume registration. The pressure registration consists of four independent pressure measurement units, which can be set to every defined pressure limit and therefore allow all pressure perfusions and allow the recognition of the smallest pressure gradients (bleeding, occlusion). The volume registration consists of an ultrasound measurement, which on the one hand registers the application of the contrast agent and on the other hand the efflux of the contrast agent. In addition, the ultrasound measurement can be connected with the venous reservoir, thereby enabling a dynamic, continuous perfusion, as the liquid is determined and quantified via the ultrasound detection (see perfusion concept).

The computer unit comprises a user module and primarily serves for data registration purposes (pressure sensors, ultrasound and pump functions of the roller pump), which are detected by the aid of a memory card and can be subsequently visualized in defined programs. This process can be carried out during or after the postmortem perfusion, or it can be printed out as a hand protocol. On the memory card and/or the computer unit, different types of process management can be automatically pre-determined, that means that on the memory card and/or the computer unit, software can be stored, which automatically controls the process management, possibly after the setting of several parameters by the user.

Furthermore, the possibility exists to directly control and refine the postmortem perfusion by the aid of empirically collected data. In addition, the postmortem perfusion can be automated on empirically validated data and ultimately standardized (see validation concept).

Expendable material: The expendable material comprises, among others, two different plastic tube types (silicone, polyethylene), and a hard shell reserve, as well as two types of cannula (venous, arterial), and different connectors (the canulla sizes and the corresponding canulla types are dependent on the corresponding perfusion method). The tube type of silicone is used as a drive tube for the roller pump and corresponds essentially to the length of the roller pump circumference. The drive tube dimensions are variable and have an external diameter of between $3/16$-$1/2$-inches (whole body- or selective organ perfusion). The remaining tube connections consist of polyethylene and have an external diameter of $1/4$-inch. The expendable material is arranged as in a conventional perfusion. The polyethylene tube is connected as a so-called venous inlet with the reservoir via the venous cannula and a connector. Parallel, an additional tube is connected with the venous cannula via a Y-connector. This tube serves for discarding the primary postmortem perfusate (coagulated blood). The outlet of the reservoir is connected with the silicone tube, which itself is guided into the roller pump and thereby empties the reservoir during operation. From the pump outlet, the silicone tube is connected via a connector with an additional polyethylene tube and connected with the arterial cannula via a connector having a Luer-Lock (contrast agent inlet). The perfusate is guided into the reservoir with a special fill line.

Perfusion Concept, Static Clinical Angiography Vs. Postmortem Dynamic Perfusion Angiography:

Static clinical angiography: Today, different angiography methods are used clinically. The most prevalent are arteriography, phlebography, coronary angiography, as well as varicography. The aim therein is to obtain an angiogram, which represents the filled inner cavity of a vessel and by which different diagnostic conclusions can be made with respect to different vascular diseases (KHK, carotis stenoses, PAVK, vessel deformations, thromboses, varices, vessel injuries).

In clinical angiography, the contrast agent is injected into the vascular system with a catheter. The cardiovascular system therein works as a "motor" for the distribution of the contrast agent. The imaging is thus only possible during the corresponding circulation time and leads to an antegrade representation in arteriography or in coronary angiography (i.e. measurement exclusively in the direction of the natural blood flow). Also in phlebo- or varicography, the contrast agent is introduced into the venous vascular system during the corresponding circulation time, and the sequence of images is taken in the antegrade (normal) blood flow. The angiography methods described above thus are static methods, which do not result in any quantitative flow data, and only the occlusion rate of single vessels can be indicated in %.

Dynamic postmortem angiography: In the real dynamic postmortem angiography, the "motor", thus the cardio-vascular system, is replaced by a roller pump. By loss or replacement of the natural heart activity, the vascular system can be filled and represented in an antegrade or, for the first time, also retrograde manner (against the normal blood flow). Vascular pathologies therefore can be looked at and represented from the "front" or from the "rear". This has relevant character, as for example a coronary thrombus, which is interpreted as a subtotal stenosis in the antegrade imaging, can be rinsed out and visualized in a retrograde manner. In addition, a severe vascular injury can even be quantified via a double cannulation (arterial-venous): Therein, a defined quantity of a defined contrast agent is introduced via the arterial cannula, and collected again via a venous cannula, wherein the difference between the inflow and outflow results in the quantity of blood loss, which can be calculated from the determinants of number of revolutions of the pump, tube diameter and time.

Most substantial differences between the two methods: Principally, all conventional angiography methods can also be carried out by the postmortem perfusion. The fundamentally different possibilities of the two methods, however, allow a new dimension of vessel imaging. For the first time, a constriction of an artery for example can also be viewed and represented distal from the stenosis, which is impossible in the static perfusion on the living body.

A second essential point is the "motor" of the postmortem perfusion. This can be linked and operated via a computer. The circulation of the contrast agent thus can be influenced almost arbitrarily, which of course is not possible on the living body. This for example allows, after a defined validation phase and the comparison of empirically-evaluated data from heart surgery, a punctual control of the pump and thus enables an exact quantification of the stenosis- or bleeding rates. The pressure gradients over the used arterial and venous cannulas of the healthy vessel with a defined quantity of volume, which was applied over the roller pump, are deemed to be empirically-evaluated data. The data thus obtained are deemed to be "norm values" and are confronted with the data obtained from the postmortem perfusion. The pressure differences are then used for the exact control of the roller pump.

Furthermore, it shall be stressed that, contrary to the measurements on the living body, not only the circulation of the contrast agent or of the entire circulation agent, respectively, can be adjusted almost arbitrarily in the sense of a desired measurement, but also other parameters. For example, the circulation rate or the circulation pressure, respectively, can also be adjusted depending on the measurement, or the progress of the measurement, respectively, such that for example in a batch-wise introduction of contrast agent a reduction of speed or a reduction of pressure, respectively, can be effected in that moment, in which the analysis device registers the entrance of the contrast agent into the area mainly examined. It is possible to make measurements at a constant pressure (that means, not in the naturally pulsed manner of flow), and thereby, for example to obtain exact data for the conditions at a maximal blood pressure and at minimal blood pressure of the circulation. Furthermore, it is, however, also possible, for example, to allow the circulation agent and the contrast agent contained therein to circulate at different temperatures. Thereby, e.g. the viscosity, but also the streaming behavior, etc. can be influenced.

This results, in summary, among others, in the following differences:

| Clinical angiography: | Postmortem angiography: |
|---|---|
| Antegrade perfusion | retrograde perfusion |
| inconstant (heart, pulsed, flow-controlled) | constant (pump, pressure-controlled) |
| static (circulation time) | dynamic |
| inflow method | in- and outflow method |
| qualitative method | quantitative method |

The invention claimed is:

1. A contrast agent for postmortem, experimental or diagnostic angiography and for examination of animal or human corpses or components thereof, comprising:
    an essentially oil-based, non-polar contrast component for X-ray examinations, said contrast component having a contrast component viscosity in the range of 30-100 mPas,
    wherein the contrast component is present in a mixture with at least one first further non-polar component of a viscosity, which is lower or at the most equal to the contrast component viscosity, and a second further non-polar component having a viscosity in the range of 25-80 mPas,
    wherein the contrast agent is essentially free from water,
    wherein the first further non-polar component is hexadecane or tetradecane, and
    wherein the contrast component and the second further non-polar component are used in a ratio of 1:5 and the first further non-polar component is used in a ratio of 50:1 to the mixture of the contrast component and the second further non-polar component.

2. The contrast agent according to claim 1, wherein the contrast component has a viscosity in the range of 30-80 mPas.

3. The contrast agent according to claim 2, wherein the contrast component is an iodine-based or sulphur-based radiographic contrast agent.

4. The contrast agent according to claim 2, wherein the contrast component is an iodized or brominated component or oil.

5. The contrast agent according to claim 1, wherein the contrast component is selected from the group consisting of a propyliodone, a fatty-acid-ethyl ester of iodized poppy-seed oil, and an iodipine.

* * * * *